United States Patent
Reeves et al.

(10) Patent No.: US 9,079,832 B2
(45) Date of Patent: Jul. 14, 2015

(54) PROCESS FOR MAKING N-SULFINYL α-AMINO AMIDES

(71) Applicants: Jonathan Timothy Reeves, New Milford, CT (US); Chris H. Senanayake, Brookfield, CT (US)

(72) Inventors: Jonathan Timothy Reeves, New Milford, CT (US); Chris H. Senanayake, Brookfield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 64 days.

(21) Appl. No.: 14/072,352

(22) Filed: Nov. 5, 2013

(65) Prior Publication Data

US 2014/0171641 A1   Jun. 19, 2014

Related U.S. Application Data

(60) Provisional application No. 61/728,977, filed on Nov. 21, 2012.

(51) Int. Cl.
| | | |
|---|---|---|
| C07C 313/06 | (2006.01) | |
| C07D 319/18 | (2006.01) | |
| C07D 295/185 | (2006.01) | |
| C07C 327/46 | (2006.01) | |

(52) U.S. Cl.
CPC ............. *C07C 313/06* (2013.01); *C07C 327/46* (2013.01); *C07D 295/185* (2013.01); *C07D 319/18* (2013.01); *C07C 2101/02* (2013.01); *C07C 2101/04* (2013.01); *C07C 2103/74* (2013.01); *C07C 2103/94* (2013.01)

(58) Field of Classification Search
CPC   C07C 313/06; C07C 327/46; C07C 2104/04; C07C 2103/74; C07C 2103/94; C07C 2101/02; C07D 295/185; C07D 319/18
USPC ...................... 564/74, 101; 549/362; 548/540; 544/160
See application file for complete search history.

(56) References Cited

U.S. PATENT DOCUMENTS

| | | | | |
|---|---|---|---|---|
| 6,894,189 | B2 * | 5/2005 | Senanayake et al. | 564/248 |
| 7,129,378 | B2 * | 10/2006 | Han et al. | 564/248 |
| 7,256,297 | B2 * | 8/2007 | Senanayake et al. | 548/122 |
| 8,222,264 | B2 | 7/2012 | Fuchs et al. | |
| 8,426,607 | B2 | 4/2013 | Fuchs et al. | |
| 8,450,308 | B2 | 5/2013 | Dillard et al. | |
| 8,633,212 | B2 | 1/2014 | Cacatian et al. | |
| 8,664,388 | B2 | 3/2014 | Fuchs et al. | |
| 2013/0053377 | A1 | 2/2013 | Dillard et al. | |
| 2013/0289050 | A1 | 10/2013 | Bukhtiyarov et al. | |
| 2013/0317014 | A1 | 11/2013 | Dillard et al. | |
| 2014/0057927 | A1 | 2/2014 | Bukhtiyarov et al. | |

FOREIGN PATENT DOCUMENTS

| | | |
|---|---|---|
| WO | 2009007300 A2 | 1/2009 |
| WO | 2009092566 A1 | 7/2009 |
| WO | 2010021680 A2 | 2/2010 |
| WO | 2010105179 A2 | 9/2010 |
| WO | 2011106414 A1 | 9/2011 |
| WO | 2013134085 A1 | 9/2013 |
| WO | 2013169531 A1 | 11/2013 |
| WO | 2014035860 A1 | 3/2014 |

OTHER PUBLICATIONS

Han et al, Journal of Organic Chemistry, 2011, 76(13), 5480-4.*
International Search Report and Written Opinion for PCT/US2013/068488 mailed May 15, 2014.
Mabic, S. et al., "Synthesis of enantiomerically pure ethylenediamines from chiral sulfinimines: a new twist to the Strecker reaction." Tetrahedron, 2001, vol. 57, No. 42, pp. 8861-8866.
Nemoto, H. et al., "Highly diastereoselective nucleophilic addition reactions of masked acyl cyanide reagents to tert-butanesulfiminides." Tetrahedron:Asymmetry, 2007, vol. 18, No. 3, pp. 383-389.
Reeves, J. et al., "Carbamoyl Anion Addition to N-Sulfinyl Imines: Highly Diastereoselective Synthesis of a-Amino Amides." Journal of the American Chemical Society, 2013, vol. 135, No. 15, pp. 5565-5568.

* cited by examiner

*Primary Examiner* — Shailendra Kumar
(74) *Attorney, Agent, or Firm* — Michael P. Morris; Atabak R. Royaee

(57) ABSTRACT

Disclosed is a process for making diastereomeric N-sulfinyl α-amino amides by reaction of chiral sulfinimines with formamides and lithium diisopropylamide. The process of the invention provides the N-sulfinyl α-amino amides in high yields and with high diastereoselectivity.

13 Claims, No Drawings

PROCESS FOR MAKING N-SULFINYL α-AMINO AMIDES

This application claims benefit of 61/728,977, filed on Nov. 21, 2012.

FIELD OF THE INVENTION

The invention relates to a process for making diastereomeric N-sulfinyl α-amino amides by reaction of chiral sulfinimines with formamides and lithium diisopropylamide. The process of the invention provides the N-sulfinyl α-amino amides in high yields and with high diastereoselectivity.

BACKGROUND OF THE INVENTION

N-sulfinyl α-amino amides can be synthesized by the Strecker process [see, e.g., S. Mabic et al., *Tetrahedron* 57: 8861-8866 (2001); A. Plant et al., *J. Org. Chem.* 73: 3714-3724 (2008); F. A. Davis et al., *J. Org. Chem.* 65: 8704-8708 (2000)], which requires the use of highly poisonous cyanide anion and in which the resultant alpha-amino nitrile intermediate has to be hydrolyzed under harsh conditions to yield the corresponding alpha-amino amide. Because the hydrolysis of the nitrile prepared according to the Strecker process provides only a primary amide (—$CONH_2$), the Strecker process is restricted to the synthesis of primary amides only.

The invention provides a highly diastereoselective process for making the N-sulfinyl α-amino amides of formula (I) which avoids the disadvantages of the Strecker synthesis.

It is known that the deprotonation of dialkylformamides (or dialkylthioformamides) affords carbamoyllithiums (or thiocarbamoyl lithiums). These carbamoyllithiums can then react with carbonyl electrophiles, thus allowing for the introduction of a carbamoyl group into carbonyl compounds. (See, e.g., D. Enders et al., *Angew. Chem. Internat. Ed.* 12:1014-1015 (1973) and B. Bánhidai et al. *Angew. Chem. Internat. Ed.* 12:836-836 (1973)). Reaction of carbamoyllithiums with sulfinimines as electrophiles has not been reported.

The inventors have found that carbamoyllithiums react with chiral, sterically hindered sulfinimines in a stereospecific manner to afford diastereomeric N-sulfinyl α-amino amides, which are useful as chiral building blocks for preparing pharmaceuticals.

BRIEF SUMMARY OF THE INVENTION

In its broadest embodiment ("Embodiment 1"), the invention relates to a process of making compounds of formula (I),

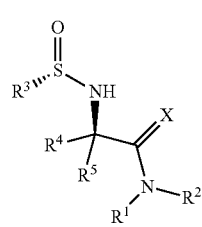

the process comprising reacting a compound of formula (II):

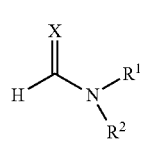

with lithium diisopropylamide to provide a first intermediate; and
reacting the first intermediate with an enantiomerically pure compound of formula (III):

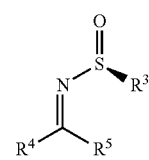

to provide the compound of formula (I), wherein
X is selected from oxygen and sulfur;
$R^1$ and $R^2$ are each independently selected from $C_{1-6}$-alkyl and phenyl;
or
$R^1$ and $R^2$ may join to form a group selected from cyclopentyl, cyclohexyl, and a 5- to 6-membered heterocycloalkyl;
$R^3$ is t-butyl or 2,4,6-triisopropylphenyl;
$R^4$ is selected from H, $C_{1-6}$-alkyl, $C_{3-6}$-cycloalkyl, carbocyclyl, phenyl, and 2,3-dihydrobenzo[b][1,4]dioxinyl; wherein each of the foregoing $C_{1-6}$-alkyl, $C_{3-6}$-cycloalkyl, carbocyclyl, phenyl and 2,3-dihydrobenzo[b][1,4]dioxinyl of said $R^4$ group is optionally substituted by 1 to 3 $R^6$ groups;
$R^5$ is selected from t-butyl, phenyl, phenyl-C≡C(R)—, and phenyl-C≡C—; wherein each of the foregoing t-butyl, phenyl, phenyl-C≡C(R)—, and phenyl-C≡C— of said $R^5$ group is optionally substituted by 1 to 3 $R^6$ groups;
or
$R^4$ and $R^5$ may join to form a group selected from cyclobutyl, cyclopentyl, cyclohexyl or dihydroindenyl, wherein each of the foregoing cyclobutyl, cyclopentyl, cyclohexyl or dihydroindenyl groups may be optionally substituted by 1 to 3 $R^6$ groups; and/or each of said cyclobutyl, cyclopentyl, cyclohexyl and dihydroindenyl groups may additionally be substituted by a 6-member spirocycloalkyl optionally substituted by 1 to 3 $R^7$ groups;
each $R^6$ is independently selected from halo, hydroxyl, $C_{1-6}$-alkyl, and $C_{1-6}$-alkyl-O—; and
each $R^7$ is independently selected from halo, hydroxyl, $C_{1-6}$-alkyl, and $C_{1-6}$-alkyl-O—.

DETAILED DESCRIPTION OF THE INVENTION

Abbreviations

DCM=dichloromethane
DMF=dimethyl formamide
LDA=lithium diisopropylamide
MTBE=methyl tert-butyl ether
THF=tetrahydrofuran As noted above, the invention relates to methods of making compounds of formula (I) by reacting a formamide (X═O) or thioformamide (X═S) of formula (II) with LDA in the presence of a sulfinimine compound of formula (III) (hereinafter the "process of the invention").

Embodiment 2

In another embodiment, the invention relates to a process of making the compound of formula (I) as described in Embodiment 1, wherein X is sulfur.

Embodiment 3

In another embodiment, the invention relates to a process of making the compound of formula (I) as described in Embodiment 1 or 2 above, wherein the compound of formula (II) is N,N-dimethylmethanethioamide.

Embodiment 4

In another embodiment, the invention relates to a process of making the compound of formula (I) as described in Embodiment 1, wherein X is oxygen.

Embodiment 5

In another embodiment, the invention relates to a process of making the compound of formula (I) as described in Embodiment 1 or 4, wherein the compound of formula (II) is selected from dimethyl formamide, diethyl formamide, isopropyl formamide, diphenyl formamide, pyrrolidine-1-carbaldehyde, and morpholine-4-carbaldehyde.

Embodiment 6

In another embodiment, the invention relates to a process of making the compound of formula (I) as described in any one of Embodiments 1 to 5, wherein $R^3$ is t-butyl.

Embodiment 7

In another embodiment, the invention relates to a process of making the compound of formula (I) as described in any one of Embodiments 1 to 5, wherein $R^3$ is 2,4,6-triisopropylphenyl.

Embodiment 8

In another embodiment, the invention relates to a process of making the compound of formula (I) as described in any one of Embodiments 1 to 7, wherein:
$R^4$ is selected from H, $C_{1-6}$-alkyl, $C_{3-6}$-cycloalkyl, carbocyclyl, and phenyl; wherein each of the foregoing $C_{1-6}$-alkyl, $C_{3-6}$-cycloalkyl, carbocyclyl, and phenyl $R^4$ groups is optionally substituted by 1 to 3 $R^6$ groups; and
$R^5$ is selected from t-butyl, phenyl, —C=C(R)-phenyl, and —C≡C-phenyl; wherein each of the foregoing $R^5$ groups is optionally substituted by 1 to 3 $R^6$ groups.

Embodiment 9

In another embodiment, the invention relates to a process of making the compound of formula (I) as described in any one of Embodiments 1 to 8, wherein $R^4$ is hydrogen.

Embodiment 10

In another embodiment, the invention relates to a process of making the compound of formula (I) as described in any one of Embodiments 1 to 8, wherein $R^4$ is selected from t-butyl, trifluoromethyl, cyclopropyl, cyclohexyl, phenyl, and a group of formula 9-A,

9-A wherein each of the foregoing $R^4$ group is optionally substituted by 1 to 3 $R^6$ groups.

Embodiment 11

In another embodiment, the invention relates to a process of making the compound of formula (I) as described in any one of Embodiments 1 to 7, wherein $R^4$ and $R^5$ join to form a group selected from cyclobutyl, cyclopentyl, cyclohexyl or dihydroindenyl, wherein each of the foregoing cyclobutyl, cyclopentyl, cyclohexyl or dihydroindenyl groups may be optionally substituted by 1 to 3 $R^6$ groups; and/or each of said cyclobutyl, cyclopentyl, cyclohexyl and dihydroindenyl groups may additionally be substituted by a 6-member spirocycloalkyl optionally substituted by 1 to 3 $R^7$ groups.

Embodiment 12

In another embodiment, the invention relates to a process of making the compound of formula (I) as described in any one of Embodiments 1 to 7 or 11, wherein $R^4$ and $R^5$ join to form the group:

Embodiment 13

In another embodiment, the invention relates to a process of making the compound of formula (27):

27 the process comprising reacting N,N-diethylformamide with lithium diisopropylamide in the presence of a compound of formula (26):

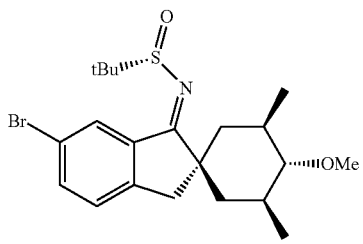

to provide the compound of formula (27).

GENERAL DEFINITIONS

Halogen:

The term halogen generally denotes fluorine, chlorine, bromine and iodine.

Alkyl:

The term "$C_{1-6}$-alkyl", either alone or in combination with another radical denotes an acyclic, saturated, branched or linear hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

Cycloalkyl:

The term "$C_{3-6}$-cycloalkyl", either alone or in combination with another radical denotes a cyclic, saturated, unbranched hydrocarbon radical with 3 to n C atoms. For example the term $C_{3-6}$-cycloalkyl includes cyclopropyl, cyclobutyl, cyclopentyl, cyclohexyl.

Carbocyclyl:

The term "carbocyclyl" as used either alone or in combination with another radical, means a mono- bi- or tricyclic ring structure consisting of 3 to 14 carbon atoms. The term "carbocycle" refers to fully saturated and aromatic ring systems and partially saturated ring systems. The term "carbocycle" encompasses fused, bridged and spirocyclic systems. Nonlimiting examples of bicycloalkyls include bicylco[2.2.1]heptane, bicylco[2.2.1]heptene, bicyclo[3.2.1]octane, and bicyclo[3.2.1]octene,

Heterocyclyl:

The term "heterocyclyl" means a saturated or unsaturated mono- or polycyclic-ring systems including aromatic ring system containing one or more heteroatoms selected from N, O or S(O)$_r$, wherein r=0, 1 or 2, consisting of 3 to 14 ring atoms wherein none of the heteroatoms is part of the aromatic ring. The term "heterocycle" is intended to include all the possible isomeric forms. Non-limiting examples of 5-6-membered heterocycloalkyl include tetrahydrofuranyl, azetidinyl, pyrrolidinyl, pyranyl, tetrahydropyranyl, dioxanyl, thiomorpholinyl, thiomorpholinyl, morpholinyl, piperidinyl, and piperazinyl.

The symbol $$\xi\!-\!R$$

means the point of attachment of a group R to a moiety.

Scheme 1 below depicts the addition of formamide (and thioformamide anions) to tert-butanesulfinimines according to the process of the invention.

Scheme 1

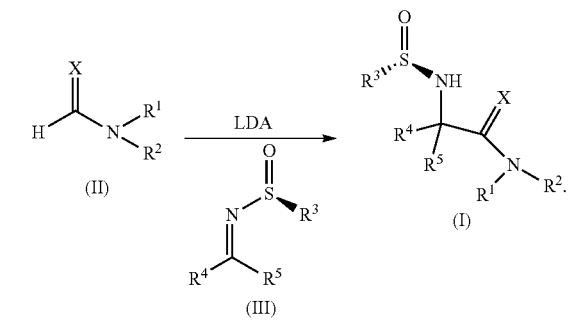

In the process of the invention, LDA reacts with the compound of formula (II) to form a first intermediate (carbamoyllithium) ("the lithiation step"). Typically, the first intermediate in not isolated. The first intermediate then reacts with the compound of formula (III). In one embodiment, the LDA is reacted with the compound of formula (II) in the absence of the compound of formula (III), and the resulting first intermediate is reacted with the compound of formula (III). In another embodiment, the LDA is reacted with the compound of formula (II) in the presence of the compound of formula (III).

The compounds of formula (II) are generally available from commercial sources or can be made be known methods (see e.g., Gibson, H. W. Chem. Rev. 1969, 69, 673-692).

The LDA used in the process of the invention may be obtained commercially or generated immediately prior to use by reaction of i-Pr$_2$NH with a lithium alkyl, e.g., n-BuLi.

The lithiation step is carried out in anhydrous, aprotic solvent. Non-limiting examples of suitable solvents for carrying this step include toluene, THF, diethyl ether, MTBE and mixtures thereof. In a one embodiment, the lithiation step is carried out in a solvent comprising toluene.

As noted above, the lithiation step may be carried out in the absence or presence of a compound of formula (III). When absent during the lithiation step, the compound of formula (III) is subsequently reacted with the admixture comprising the carbamoyllithium. It will be understood that when the compound of formula (III) is absent during the lithiation step, the compound of formula (III) can be added to the to the reaction carbamoyllithium admixture, or the carbamoyllithium admixture can be added to the compound of formula (III), or the compound of formula (III) and the carbamoyllithium admixture can mixed together simultaneously. When the absent during the lithiation step, the compound of formula (III) may be used neat; alternatively, the compound of formula (III) may be a component of a suspension or solution comprising the anhydrous, aprotic solvents described above for the lithiation step.

The process of the invention is carried out for a time and at a temperature sufficient to provide the compound of formula (I). The process of the invention is typically carried out at a temperature from about −78° C. to about the refluxing point of the solvent. In one embodiment, the reaction of the compound of formulae (II) and LDA, optionally in the presence of the compound of formula (III), is carried out at a temperature from about −78° C. to 30° C.; more preferably from −78° C. to about 0° C.

In one embodiment, the process of the invention relates to methods of making compounds of formula (I) wherein $R^4$ for the compounds of formula (III) and formula (I) is hydrogen. Compounds of formula (III) where $R^4$ is hydrogen are referred to herein as sulfinyl aldimines. When the compound of formula (III) is a sulfinyl aldimine, the Inventors found that the selectivity is sensitive to the steric bulkiness of both the LDA and the sulfinyl aldimine. For example, the addition of DMF anion to pivaldehyde derived imine 1 gave the tert-leucine amide 2 in 92:8 selectivity (see Table 1, Example 1). When using the bulkier diisopropylformamide, the resulting amide 3 is obtained in much higher selectivity (>95:5; see Table 1, Example 2). Alternatively, the use of the more bulky 2,4,6-triisopropylphenylsulfinimine 4 in combination with DMF anion also provided a product 5 with higher selectivity (98:2; see Table 1, Example 3) than was obtained with the less sterically demanding compound 1 (92:8; see Table 1, Example 1). Likewise, the addition of diethylformamide to sulfinimine 10 gave the product in 90:10 diastereoselectivity (see Table 1, Example 6) whereas an analogous reaction with the more sterically demanding 2,4,6-triisopropylphenyl-sulfinimine 12 gave the product in higher selectivity (95:5; see Table 1, Example 7).

TABLE 1

Formamide anion addition to sulfinyl aldimines (where $R^4$ is hydrogen)[a]

| Ex. | Sulfinimine | Formamide | Product (yield)[b] | dr[c] |
| --- | --- | --- | --- | --- |
| 1 | 1 (t-Bu sulfinyl imine of pivaldehyde) | Me₂NCHO | 2 (72%) t-Bu-S(O)-NH-C(t-Bu)H-C(O)-NMe₂ | 92:8 |
| 2 | 1 (t-Bu sulfinyl imine of pivaldehyde) | i-Pr₂NCHO | 3 (74%) t-Bu-S(O)-NH-C(t-Bu)H-C(O)-N(i-Pr)₂ | >95:5 |
| 3 | 4[d] (TIPP sulfinyl imine of pivaldehyde) | Me₂NCHO | 5 (83%) TIPP-S(O)-NH-C(t-Bu)H-C(O)-NMe₂ | 98:2 |
| 4 | 6 (t-Bu sulfinyl imine of Me₂N-CH₂-C(Me)₂-CHO) | morpholine-CHO | 7 (76%) t-Bu-S(O)-NH-C(CH₂NMe₂, Me₂)-C(O)-morpholine | 93:7 |

TABLE 1-continued

Formamide anion addition to sulfinyl aldimines (where $R^4$ is hydrogen)[a]

| Ex. | Sulfinimine | Formamide | Product (yield)[b] | dr[c] |
|---|---|---|---|---|
| 5 | 8 | Ph$_2$NCHO | 9 (85%) | 96:4 |
| 6 | 10 | Et$_2$NCHO | 11 (83%) | 90:10 |
| 7 | 12[d] | Et$_2$NCHO | 13 (85%) | 96:4 |

[a]Typical reaction conditions: 1 equiv sulfinimine, 3.1 equiv formamide, 3 equiv LDA, PhMe, −78° C.
[b]Isolated yield after chromatography on SiO$_2$.
[c]Diastereomeric ratio determined from either HPLC or $^1$H NMR of crude reaction mixture.
[d]TIPP = 2,4,6-triisopropylphenyl.

In another embodiment, the process of the invention relates to making compounds of formula (I) wherein $R^4$ for the compounds of formula (III) and formula (I) is a group other than hydrogen. Compounds of formula (III) where $R^4$ is a group other than hydrogen are referred to herein as sulfinyl ketimines. When the compound of formula (III) is a sulfinyl ketimine, Applicants found that the process of the invention also proceeds with high diastereoselectivity for a variety of ketimine substrates (see Table 2). Sterically demanding α-quaternary ketimines reacted to give α-quaternary β-quaternary amino amides in high diastereoselectivities (Examples 8-10 and 13 in Table 2). The enolizable ketimine 20 gave a low conversion under the standard reaction conditions, likely due to competitive enolization of the substrate on addition of LDA. However, generation of the carbamoyllithium using tert-butyllithium, and subsequent addition of ketimine 20 provided the product 21 with >90% conversion, >95:5 diastereoselectivity, and an isolated yield of 77% (Example 11, Table 2). The α,β-unsaturated ketimine 22 reacted exclusively to give the 1,2-addition product 23 with 92:8 diastereoselectivity (Example 12, Table 2). An alkynyl ketimine also reacted smoothly with N-formylpyrrolidine to provide the amino amide 25 (diastereoselectivity=94:6) (Example 13, Table 2). The reaction of cyclic ketimine 26 with LDA provided the cyclic product 27 in good yield (81%) and with high diastereoselectivity (95:5; Example 14, Table 2).

TABLE 2

Formamide anion addition to sulfinyl ketimines (where R⁴ is a group other than hydrogen)$^a$

| Ex. | Sulfinimine | Formamide | Product (yield)$^b$ | dr$^c$ |
|---|---|---|---|---|
| 8 | 14 (t-Bu-S(O)-N=C(4-F-C₆H₄)(1-adamantyl)) | Et₂NCHO | (t-Bu-S(O)-NH-C(4-F-C₆H₄)(1-adamantyl)-C(O)NEt₂) | >95:5 |
| 9 | 16 (t-Bu-S(O)-N=C(Ph)(C(cyclohexyl)(4-MeO-C₆H₄))) | Et₂NCHO | 17 (75%) | >95:5 |
| 10 | 18 (t-Bu-S(O)-N=C(4-Br-C₆H₄)(1-methylcyclopropyl)) | Me₂NCHO | 19 (70%) | 95:5 |
| 11 | 20 (t-Bu-S(O)-N=C(Ph)(cyclopropyl)) | i-Pr₂NCHO | 21 (77%) | >95:5 |
| 12 | 22 (t-Bu-S(O)-N=C(Ph)(CH=CH-Ph)) | morpholine-NCHO | 23 (67%) | 92:8 |
| 13 | 24 (t-Bu-S(O)-N=C(t-Bu)(C≡C-Ph)) | pyrrolidine-NCHO | 25 (73%) | 94:6 |

TABLE 2-continued

Formamide anion addition to sulfinyl ketimines (where $R^4$ is a group other than hydrogen)[a]

| Ex. | Sulfinimine | Formamide | Product (yield)[b] | dr[c] |
|---|---|---|---|---|
| 14 | 26 | Et$_2$NCHO | 27 (76%) | 97:3 |
| 15 | 26 | Me$_2$NCHS | 28 (84%) | 96:4 |

[a]Typical reaction conditions: 1 equiv sulfinimine, 3.1 equiv formamide, 3 equiv LDA, PhMe, −78° C.
[b]Isolated yield after chromatography on SiO$_2$.
[c]Diastereomeric ratio determined from either HPLC or $^1$H NMR of crude reaction mixture.

As noted above, the diastereomeric compounds produced by the process of the invention can serve as building blocks for further organic compounds. For example, compounds could be conveniently converted to amino ester derivatives by employing the procedure of Heimgartner and co-workers (see Scheme 2). (See also, P. Wipf et al., *Helv. Chim. Acta* 69: 1153-1162 (1986)). For example, deprotection of the sulfinyl group of 25 with HCl and subsequent benzoylation of the amino group gave benzamide 29. Subjection of 29 to anhydrous HCl in warm toluene effected intramolecular cyclization to an intermediate oxazolone 30, which was cleaved with methanol to give the methyl ester 31. The oxazolone formation is facilitated by the strong Thorpe-Ingold effect of the sterically demanding substrate.

Scheme 2. Conversion of the amide group to an ester.

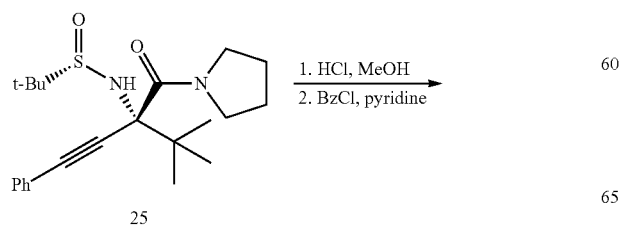

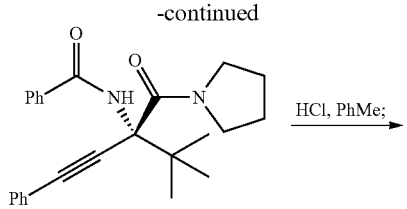

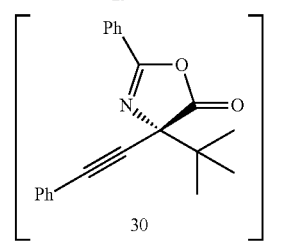

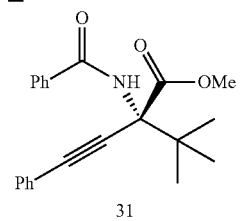

EXPERIMENTAL SECTION

General Procedure

Reaction monitoring is performed by reverse phase HPLC. Reaction diastereoselectivities are determined on crude product mixtures by either reverse phase HPLC analysis or by $^1$H NMR analysis.

Starting Materials:

Unless otherwise described, all reactants and reagents are obtained from commercial sources or made by known procedures. The sulfinimines are prepared by the general procedure described by Ellman and co-workers in this reference: Liu, G. et al; *J. Org. Chem.* 1999, 64, 1278.

Example 1

Preparation of Compound 2

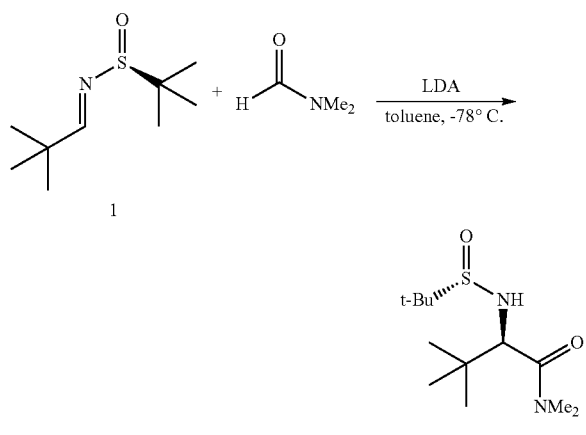

Preparation of LDA solution: A flask is charged with diisopropylamine (2.30 mL, 16.37 mmol), THF (1 mL) and toluene (5 mL). The solution is cooled to about 0° C. and treated with n-BuLi (5.96 mL, 15.85 mmol, 2.67 M/hexanes) at a rate sufficient to maintain the batch at a temperature below 10° C. The resulting solution is stirred at about 0° C. for about 15 min.

A separate flask is charged with sulfinimine 1 (1.00 g, 5.28 mmol), N,N-dimethylformamide (1.23 mL, 15.85 mmol) and toluene (10 mL), and the mixture is cooled in a dry ice/acetone bath (−78° C.). The LDA solution prepared above is added dropwise to the sulfinimine solution at −78° C. The reaction mixture is stirred at about −78° C. for about 30 min. Water (15 mL) is added, and the reaction mixture is warmed to about 25° C. Ethyl acetate (30 mL) is added and the layers are separated. The resulting organic phase is dried over sodium sulfate, filtered, and concentrated by distillation at reduced pressure to give the crude product. $^1$H NMR analysis of the crude product shows a diastereomeric ratio of 92:8. The crude product is purified by flash column chromatography on SiO$_2$ using hexanes/ethyl acetate as eluent to give the diastereomerically pure product 2 as a colorless oil which solidifies on standing to a colorless solid. Yield: 998 mg, 72.0%.

Example 2

Preparation of Compound 3

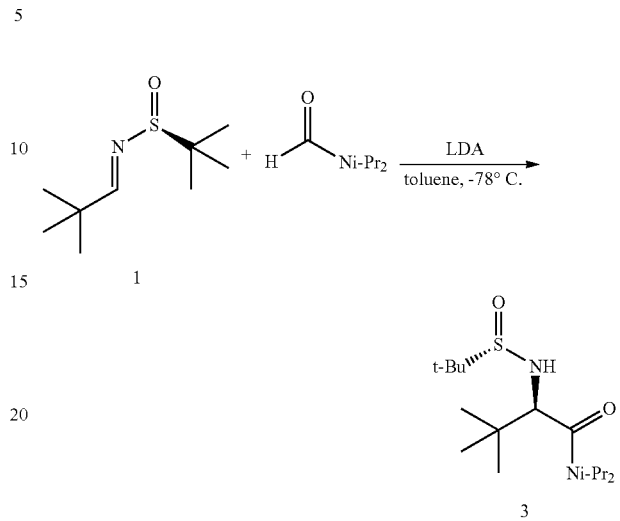

Preparation of LDA solution: A flask is charged with diisopropylamine (2.30 mL, 16.37 mmol), THF (1 mL) and toluene (5 mL). The solution is cooled to about 0° C. and treated with n-BuLi (5.96 mL, 15.85 mmol, 2.67 M/hexanes) at a rate sufficient to maintain the batch at a temperature below 10° C. The resulting solution is stirred at about 0° C. for about 15 min.

A separate flask is charged with sulfinimine 1 (1.00 g, 5.28 mmol), N,N-diisopropylformamide (2.38 mL, 16.37 mmol) and toluene (10 mL), and the mixture is cooled in a dry ice/acetone bath (−78° C.). The LDA solution prepared above is added dropwise to the sulfinimine solution at −78° C. and stirred at about −78° C. for about 30 min Water (15 mL) is added, and the reaction mixture is warmed to about 25° C. Ethyl acetate (30 mL) is added, and the layers are separated. The organic phase is dried over sodium sulfate, filtered, and concentrated by distillation at reduced pressure to give the crude product. $^1$H NMR analysis of the crude product shows a diastereomeric ratio of >95:5 (minor diastereomer not detected). The crude product is purified by flash column chromatography on SiO$_2$ using hexanes/ethyl acetate as eluent to give the diastereomerically pure product 3 as a colorless solid. Yield: 1.25 g, 74.3%.

Example 3

Preparation of Compound 5

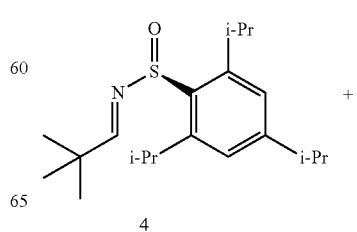

-continued

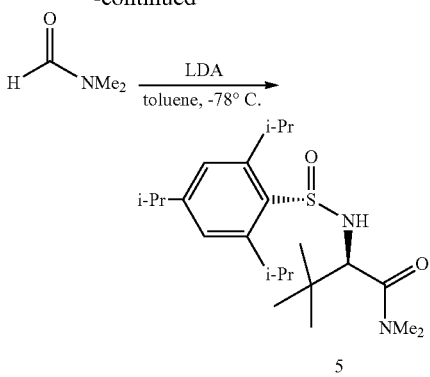

Preparation of LDA solution: A flask is charged with diisopropylamine (0.65 mL, 4.62 mmol), THF (0.5 mL) and toluene (2.5 mL) and cooled to about 0° C. The solution is treated with n-BuLi (1.67 mL, 4.47 mmol, 2.67 M/hexanes) at a rate sufficient to maintain the batch at a temperature below 10° C. The resulting solution is stirred at about 0° C. for about 15 min.

A separate flask is charged with sulfinimine 4 (500 mg, 1.49 mmol), N,N-dimethylformamide (0.36 mL, 4.62 mmol) and toluene (5 mL), and the mixture is cooled in a dry ice/acetone bath (−78° C.). The LDA solution prepared above is added dropwise to the sulfinimine solution at −78° C. The reaction mixture is stirred at about −78° C. for about 30 min. Water (10 mL) is added, and the reaction mixture is warmed to about 25° C. Ethyl acetate (20 mL) is added, and the layers are separated. The organic phase is dried over sodium sulfate, filtered, and concentrated by distillation at reduced pressure to give the crude product. HPLC analysis of the crude product shows a diastereomeric ratio of 98:2. The crude product is purified by flash column chromatography on $SiO_2$ using hexanes/ethyl acetate as eluent to give the diastereomerically pure product 5 as a colorless oil. Yield: 507 mg, 83.3%.

Example 4

Preparation of Compound 7

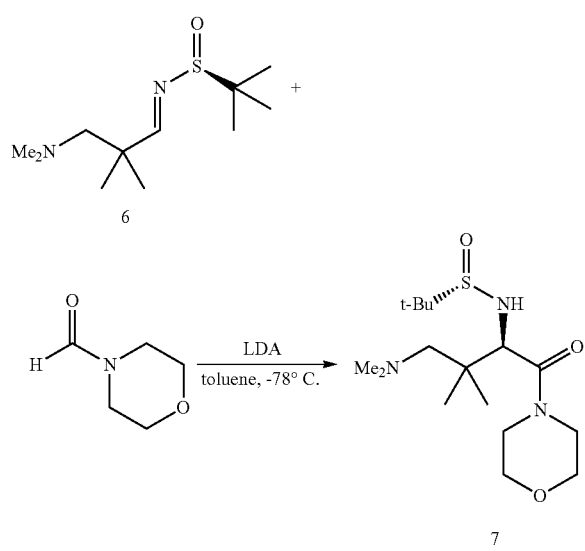

Preparation of LDA solution: A flask is charged with diisopropylamine (0.94 mL, 6.67 mmol), THF (0.5 mL) and toluene (2.5 mL). The solution is cooled to about 0° C. and treated with n-BuLi (2.43 mL, 6.46 mmol, 2.67 M/hexanes) at a rate sufficient to maintain the batch at a temperature below 10° C. The resulting solution is stirred at about 0° C. for about 15 min.

A separate flask is charged with sulfinimine 6 (500 mg, 2.15 mmol), N-formylmorpholine (0.67 mL, 6.67 mmol) and toluene (5 mL), and the mixture is cooled in a dry ice/acetone bath (−78° C.). The LDA solution prepared above is added dropwise to the sulfinimine solution at −78° C. The reaction mixture is stirred at about −78° C. for about 30 min. Water (10 mL) is added, and the reaction mixture is warmed to about 25° C. Ethyl acetate (30 mL) is added, and the layers are separated. The organic phase are dried over sodium sulfate, filtered, and concentrated by distillation at reduced pressure to give the crude product. $^1H$ NMR analysis of the crude product shows a diastereomeric ratio of 93:7. The crude product is purified by flash column chromatography on $SiO_2$ using hexanes/ethyl acetate as eluent to give the diastereomerically pure product 7 as a colorless oil. Yield: 571 mg, 76.4%.

Example 5

Preparation of Compound 9

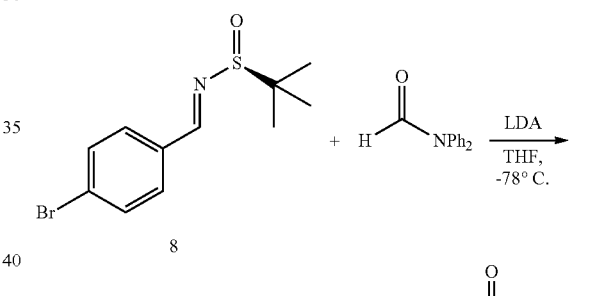

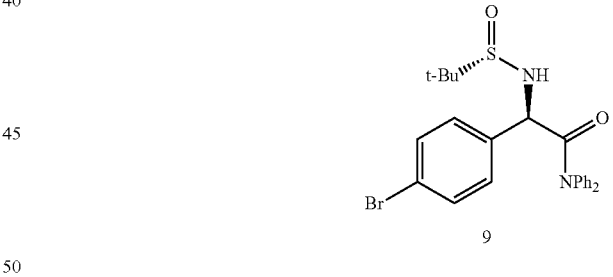

A flask is charged with sulfinimine 8 (500 mg, 1.74 mmol), N,N-diphenylformamide (684 mg, 3.47 mmol) and THF (5 mL), and the mixture is cooled in a dry ice/acetone bath (−78° C.). Commercial LDA solution (1.74 mL, 3.47 mmol, 2.0 M/THF/heptane/ethylbenzene) is added dropwise rate to the sulfinimine solution at −78° C. The reaction mixture is stirred at about −78° C. for about 30 min. Water (10 mL) is added, and the reaction mixture is warmed to about 25° C. Ethyl acetate (30 mL) is added, and the layers are separated. The organic phase is dried over sodium sulfate, filtered, and concentrated by distillation at reduced pressure to give the crude product. $^1H$ NMR analysis of the crude product shows a diastereomeric ratio of 96:4. The crude product is purified by flash column chromatography on $SiO_2$ using hexanes/ethyl acetate as eluent to give the diastereomerically pure product 9 as a white solid. Yield: 714 mg, 84.8%.

Example 6

Preparation of Compound 11

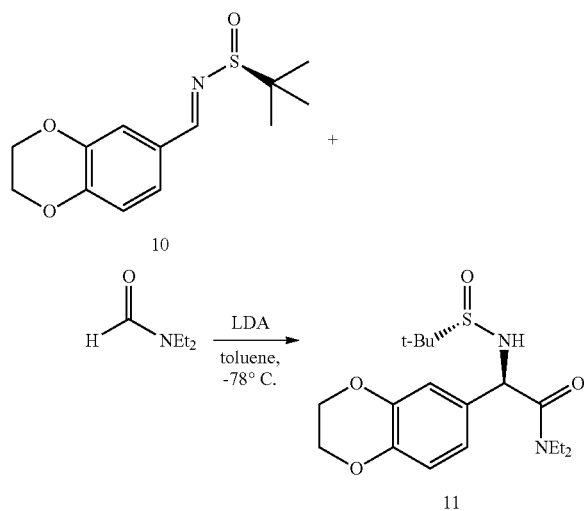

A flask is charged with sulfinimine 10 (500 mg, 1.87 mmol), N,N-diethylformamide (0.644, 5.80 mmol) and toluene (5 mL), and the mixture is cooled in a dry ice/acetone bath (−78° C.). Commercial LDA solution (2.90 mL, 5.80 mmol, 2.0 M/THF/heptane/ethylbenzene) is added dropwise to the sulfinimine solution at −78° C. The reaction mixture is stirred at about −78° C. for about 30 min. Water (10 mL) is added, and the reaction mixture is warmed to about 25° C. Ethyl acetate (30 mL) is added, and the layers are separated. The organic phase is dried over sodium sulfate, filtered, and concentrated by distillation at reduced pressure to give the crude product. $^1$H NMR analysis of the crude product shows a diastereomeric ratio of 90:10. The crude product is purified by flash column chromatography on SiO$_2$ using hexanes/ethyl acetate as eluent to give the diastereomerically pure product 11 as a colorless oil. Yield: 570 mg, 82.7%.

Example 7

Preparation of Compound 13

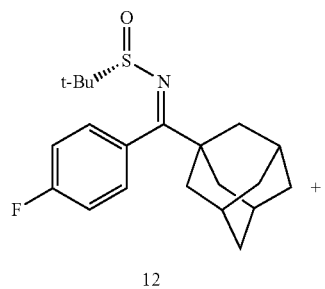

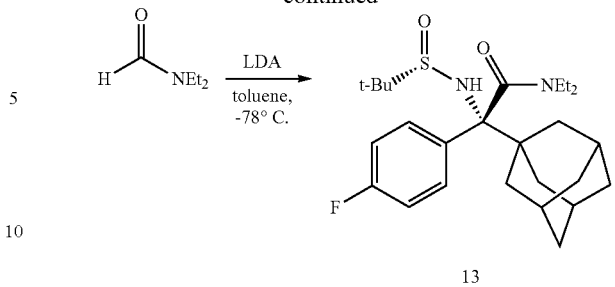

Preparation of LDA solution: A flask is charged with diisopropylamine (1.20 mL, 8.58 mmol), THF (1 mL) and toluene (5 mL). The solution is cooled to about 0° C. The solution is treated with n-BuLi (3.11 mL, 8.30 mmol, 2.67 M/hexanes) at a rate sufficient to maintain the batch at a temperature below 10° C. The resulting solution is stirred at about 0° C. for about 15 min.

A separate flask is charged with sulfinimine 12 (1.00 g, 2.77 mmol), N,N-diethylformamide (0.96 mL, 8.58 mmol) and toluene (10 mL), and the mixture is cooled in a dry ice/acetone bath (−78° C.). The LDA solution prepared above is added dropwise to the sulfinimine solution at −78° C. The reaction mixture is stirred at about −78° C. for about 30 min. Water (15 mL) is added, and the reaction mixture is warmed to about 25° C. Ethyl acetate (30 mL) is added, and the layers are separated. The organic phase is dried over sodium sulfate, filtered, and concentrated by distillation at reduced pressure to give the crude product. $^1$H NMR analysis of the crude product shows a diastereomeric ratio of 95:5. The crude product is purified by flash column chromatography on SiO$_2$ using hexanes/ethyl acetate as eluent to give the diastereomerically pure product 13 as a colorless oil which solidified on standing to a colorless solid. Yield: 1.04 g, 81.3%.

Example 8

Preparation of Compound 15

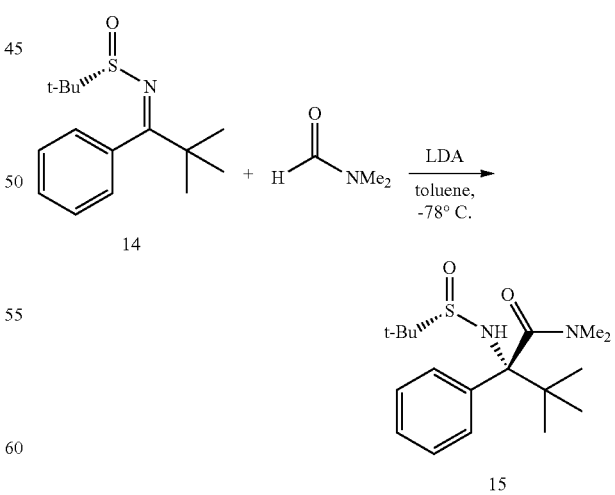

Preparation of LDA solution: A flask is charged with diisopropylamine (2.67 mL, 19.03 mmol), THF (1 mL) and toluene (5 mL). The solution is cooled to about 0° C. and treated with n-BuLi (7.08 mL, 18.84 mmol, 2.67 M/hexanes) at a rate sufficient to maintain the batch at a temperature below 10° C. The resulting solution is stirred at about 0° C. for about 15 min.

A separate flask is charged with sulfinimine 14 (500 mg, 1.88 mmol), N,N-dimethylformamide (1.47 mL, 19.03 mmol) and toluene (5 mL), and the mixture is cooled in a dry ice/acetone bath (−78° C.). The LDA solution prepared above is added dropwise to the sulfinimine solution at −78° C. The reaction mixture is stirred at about −78° C. for about 30 min. Water (15 mL) is added, and the reaction mixture is warmed to about 25° C. Ethyl acetate (30 mL) is added, and the layers are separated. The organic phase is dried over sodium sulfate, filtered, and concentrated by distillation at reduced pressure to give the crude product. ¹H NMR analysis of the crude product shows a diastereomeric ratio of >95:5 (minor diastereomer not detected). The crude product is purified by flash column chromatography on SiO₂ using hexanes/ethyl acetate as eluent to give the diastereomerically pure product 15 as a white solid. Yield: 497 mg, 77.9%.

Example 9

Preparation of Compound 17

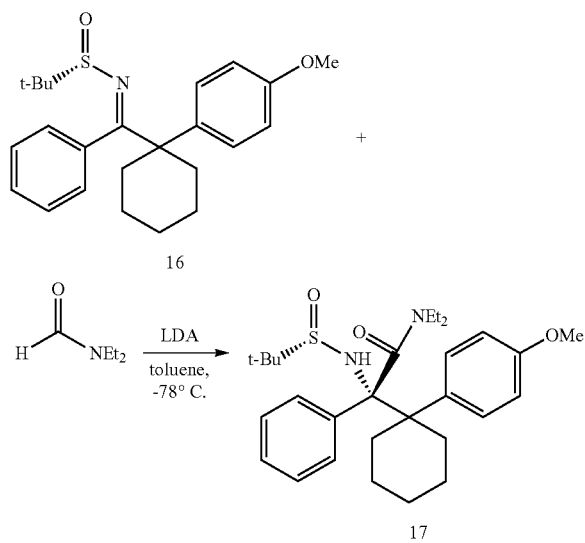

A flask is charged with sulfinimine 16 (500 mg, 1.26 mmol), N,N-diethylformamide (1.30 mL, 11.70 mmol) and toluene (5 mL), and the mixture is cooled in a dry ice/acetone bath (−78° C.). Commercial LDA solution (5.66 mL, 11.32 mmol, 2.0 M/THF/heptane/ethylbenzene) is charged dropwise to the sulfinimine solution at a rate sufficient to maintain the temperature at −78° C. The reaction mixture is stirred at about −78° C. for about 30 min. Water (15 mL) is added, and the reaction mixture is warmed to about 25° C. Ethyl acetate (30 mL) is added, and the layers are separated. The organic phase is dried over sodium sulfate, filtered, and concentrated by distillation at reduced pressure to give the crude product. ¹H NMR analysis of the crude product shows a diastereomeric ratio of >95:5 (minor diastereomer not detected). The crude product is purified by flash column chromatography on SiO₂ using hexanes/ethyl acetate as eluent to give the diastereomerically pure product 17 as a white solid. Yield: 472 mg, 75.2%.

Example 10

Preparation of Compound 19

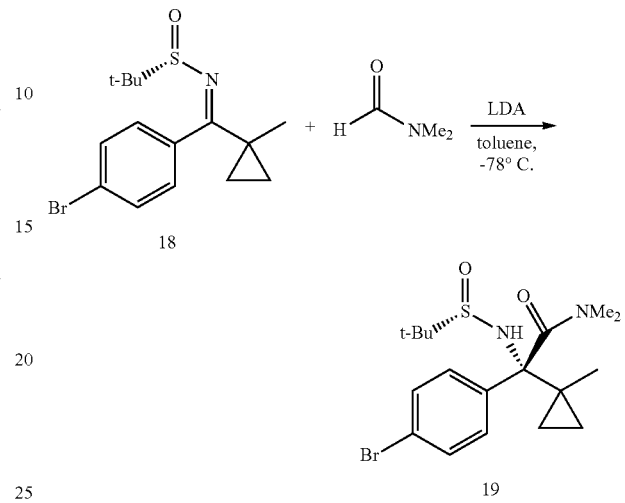

A flask is charged with sulfinimine 18 (500 mg, 1.46 mmol), N,N-dimethylformamide (0.35 mL, 4.52 mmol) and toluene (5 mL) and cooled in a dry ice/acetone bath (−78° C.). Commercial LDA solution (2.12 mL, 4.38 mmol, 2.0 M/THF/heptane/ethylbenzene) is added dropwise to the sulfinimine solution at −78° C. The reaction mixture is stirred at about −78° C. for about 30 min. Water (15 mL) is added, and the reaction mixture is warmed to about 25° C. Ethyl acetate (30 mL) is added, and the layers are separated. The organic phase is dried over sodium sulfate, filtered, and concentrated by distillation at reduced pressure to give the crude product. ¹H NMR analysis of the crude product shows a diastereomeric ratio of 95:5. The crude product is purified by flash column chromatography on SiO₂ using hexanes/ethyl acetate as eluent to give the diastereomerically pure product 19 as a white solid. Yield: 426 mg, 70.2%.

Example 11

Preparation of Compound 21

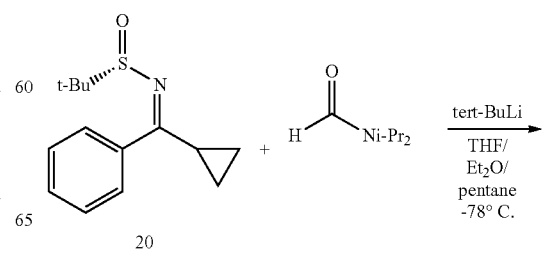

-continued

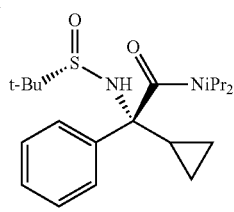

A flask is charged with N,N-diisopropylformamide (0.58 mL, 4.01 mmol), THF (20 mL), Et$_2$O (20 mL), and pentane (5 mL) and cooled in a dry ice/acetone bath (−78° C.). Tert-butyllithium solution (2.60 mL, 4.41 mmol, 1.7 M/pentane) is added dropwise to the solution at −78° C. The reaction mixture is stirred at about −78° C. for about 30 min. A solution of sulfinimine 20 (500 mg, 2.01 mmol) in THF (5 mL) is added dropwise at −78° C. The reaction mixture is stirred at about −78° C. for about 30 min. Water (15 mL) is added, and the reaction mixture is warmed to about 25° C. Ethyl acetate (30 mL) is added, and the layers are separated. The organic phase is dried over sodium sulfate, filtered, and concentrated by distillation at reduced pressure to give the crude product. $^1$H NMR analysis of the crude product shows a diastereomeric ratio of >95:5 (minor diastereomer not detected). The crude product is purified by flash column chromatography on SiO$_2$ using hexanes/ethyl acetate as eluent to give the diastereomerically pure product 21 as a white solid. Yield: 584 mg, 76.9%.

Example 12

Preparation of Compound 23

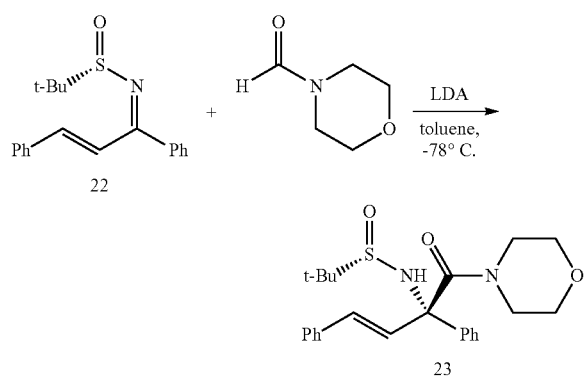

Preparation of LDA solution: A flask is charged with diisopropylamine (0.70 mL, 4.98 mmol), THF (0.5 mL) and toluene (5 mL) and cooled to about 0° C. The solution is treated with n-BuLi (1.81 mL, 4.82 mmol, 2.67 M/hexanes) at a rate sufficient to maintain the batch at a temperature below 10° C. The resulting solution is stirred at about 0° C. for about 15 min.

A separate flask is charged with sulfinimine 22 (500 mg, 1.61 mmol), N-formylmorpholine (0.50 mL, 4.98 mmol) and toluene (5 mL), and the mixture is cooled in a dry ice/acetone bath (−78° C.). The LDA solution prepared above is added dropwise to the sulfinimine solution at −78° C. The reaction mixture is stirred at about −78° C. for about 30 min. Water (15 mL) is added, and the reaction mixture is warmed to about 25° C. Ethyl acetate (30 mL) is added, and the layers are separated. The organic phase is dried over sodium sulfate, filtered, and concentrated by distillation at reduced pressure to give the crude product. $^1$H NMR analysis of the crude product shows a diastereomeric ratio of 92:8. The crude product is purified by flash column chromatography on SiO$_2$ using hexanes/ethyl acetate as eluent to give the diastereomerically pure product 23 as a white solid. Yield: 460 mg, 67.2%.

Example 13

Preparation of Compound 25

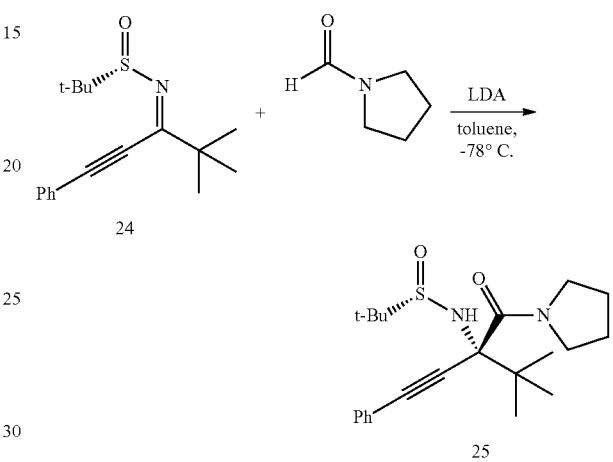

A flask is charged with sulfinimine 24 (500 mg, 1.73 mmol), N-formylpyrrolidine (1.00 mL, 10.54 mmol) and toluene (5 mL), and the mixture is cooled in a dry ice/acetone bath (−78° C.). Commercial LDA solution (5.18 mL, 10.37 mmol, 2.0 M/THF/heptane/ethylbenzene) is added dropwise to the sulfinimine solution at −78° C. The reaction mixture is stirred at about −78° C. for about 30 min. Water (15 mL) is added, and the reaction mixture is warmed to about 25° C. Ethyl acetate (30 mL) is added, and the layers are separated. The organic phase is dried over sodium sulfate, filtered, and concentrated by distillation at reduced pressure to give the crude product. $^1$H NMR analysis of the crude product shows a diastereomeric ratio of 94:6. The crude product is purified by flash column chromatography on SiO$_2$ using hexanes/ethyl acetate as eluent to give the diastereomerically pure product 25 as a light brown oil. Yield: 491 mg, 73.1%.

Example 14

Preparation of Compound 27

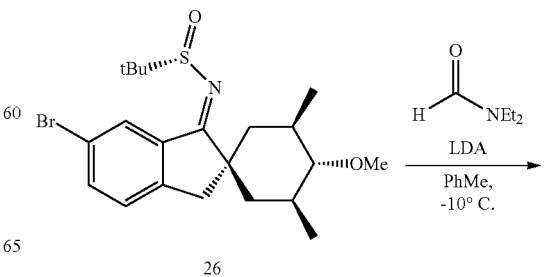

-continued

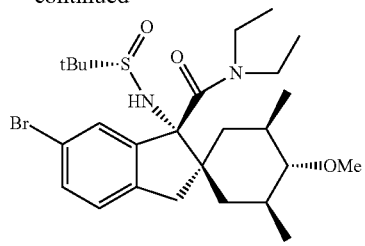

27

-continued

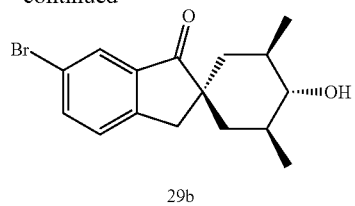

29b

A. Preparation of Compound 26:
Step 1: Synthesis of Intermediate 29a

A mixture of $FeCl_3$ (6.0 g, 37.0 mmol) with toluene (60 mL) was cooled to 0° C. A mixture of compound 29a (11.9 g, 37.0 mmol) in THF (48 mL) was then added to the mixture.

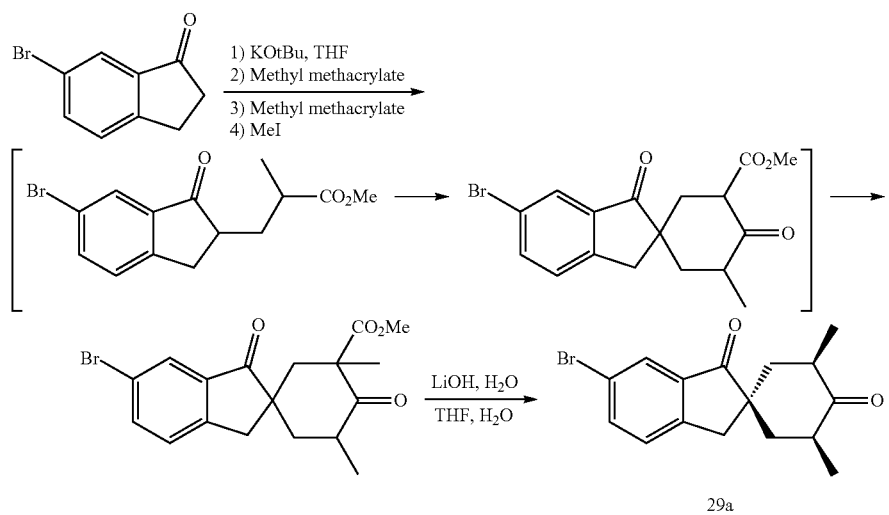

29a

To a mixture of 6-bromo-indan-1-one (100.00 g, 473.8 mmol) in anhydrous THF (1 L) at 0° C. was added t-BuOK (58.5 g, 521.2 mmol, 1.1 eq), 2 min later the mixture was warmed up to room temperature and was stirred for another 10 min before methyl methacrylate (49.8 g, 53.2 mL, 497.5 mmol, 1.05 eq) was added in one portion. After 2 h, methyl acrylate (49.0 g, 51.2 mL, 568.6 mmol, 1.2 eq) was added to the reaction mixture. After 3 h at room temperature, MeI (101 g, 44.3 mL, 710.7 mmol, 1.5 eq) was added to the reaction mixture, and it was stirred for 16 hours. $H_2O$ (1 L) was added followed by $LiOH \cdot H_2O$ (79.5 g, 1895.2 mmol, 4.0 eq), the mixture was stirred for 28 h at room temperature. THF was removed under reduced pressure. The residue was diluted with $H_2O$ (1 L) and filtered, washed with $H_2O$ until the filtrate was neutral. The product was washed with to afford 50 g of intermediate 29a.

Step 2: Synthesis of Intermediate 29b

The mixture was stirred for 5 min at 0° C. and then cooled to −10° C. A solution of t-$BuNH_2$—$BH_3$ (3.5 g, 40.7 mmol) in THF (12 mL) was added dropwise to the reaction mixture at −10° C. The reaction mixture was stirred at about −10° C. for 30 min, quenched with 6N aq HCl solution (10 mL), stirred at about 0° C. for 30 min, and then allowed to warm to room temperature. The mixture was concentrated to remove THF, and toluene (60 mL) was added. The aqueous layer was removed, and the organic phase was washed with water (3×60 mL). The organic phase was concentrated to ½ volume, heated to 50° C. to obtain a solution, and then cooled to 0° C. over 1 h and held at 0° C. for 1 h. The solid was filtered and washed with cold (0° C.) toluene (12 mL), and dried under vacuum to give compound 29b (9.93 g, 83%). LC-MS: tR=2.36 min, MS (ESI) m/z 323.0/325.0 [M+H]+.

Step 3. Synthesis of Intermediate 29c

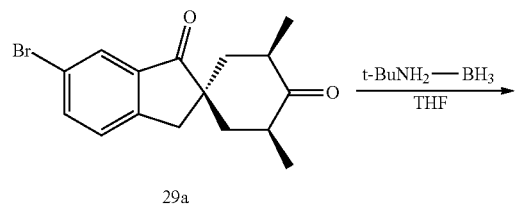

29a

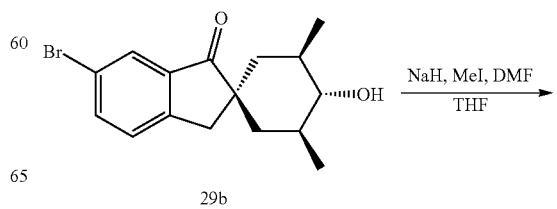

29b

-continued

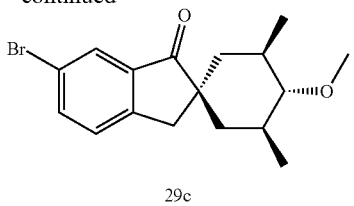

29c

To a mixture of compound 29b (20.0 g, 61.9 mmol) with DMF (200 mL) was added NaH (5.0 g, 123.8 mmol, 2.0 eq) at 0° C. Then it was stirred for 15 min at 0° C. and MeI (17.6 g, 123.8 mmol, 2.0 eq) was added at 0° C. Then it was warmed to room temperature and stirred for 1.5 h at room temperature. The mixture was quenched with H₂O and extracted with EtOAc. The combined organic phases were washed with H₂O and brine, dried, concentrated to afford crude product, which was purified by column on silica gel (eluent:petroleum ether: ethyl acetate from 100/1 to 5/1) to afford intermediate 29c (20 g, 96.2%).

Step 4. Synthesis of Compound 26

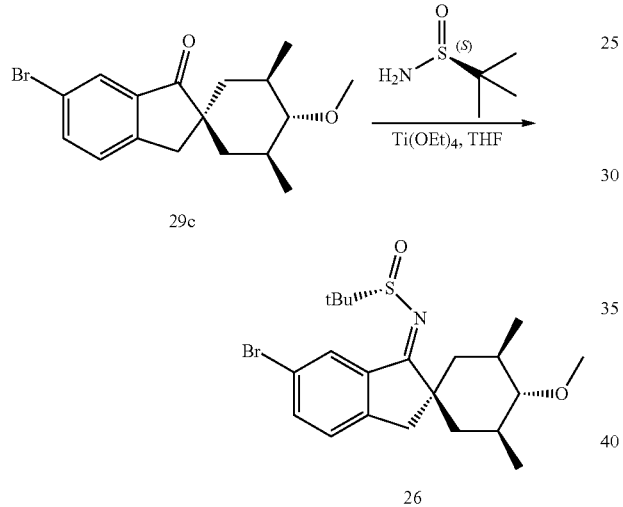

The mixture of compound 34 (20.0 g, 59.3 mmol) and titanium (IV) ethoxide (108.2 g, 474.4 mmol) in dry THF (200 ml) was stirred at room temperature for 1 hour. N-tert-butylsulfinamide (29 g, 237.2 mmol) was added. The resulting mixture was stirred at 80° C. under N₂ atmosphere overnight. The reaction mixture was then cooled and water (400 ml) was added. The mixture was filtered and the aqueous layer was extracted with ethyl acetate (3×400 mL). The separated organic phase was dried and concentrated under reduced pressure to give crude product. The residue was purified by column chromatography on silica gel (petroleum ether: ethyl acetate=20:1) to give intermediate 35 (18.4 g, 70.5%).

B. Preparation of Compound 27

A solution of sulfinimine 26 (10.0 g, 22.7 mmol) and N,N-diethylformamide (7.0 mL, 62.8 mmol) in toluene (80 mL) is cooled to −10° C. LDA solution (30.4 mL, 60.8 mmol, 2.0M in THF/heptane/ethylbenzene) is then added dropwise to the reaction mixture at −10° C. The mixture is stirred for 30 min at −10° C., quenched with water (40 mL) and then allowed to warm to room temperature. The aqueous layer is removed, and the organic phase is washed with water (40 mL). The organic phase is concentrated under vacuum at 50-60° C. to the minimum volume and treated with heptane (80 mL). The mixture is again concentrated under vacuum at 50-60° C. to the minimum volume and treated with heptane (60 mL). The mixture is allowed to cool to room temperature, further cooled to about 0° C., and held at 0° C. for about 1 hour. The solid is filtered, washed with cold (0° C.) heptane (10 mL), and dried under vacuum to (1r,1'R,3R,4R,5S)-6'-bromo-1'-((S)-1,1-dimethylethylsulfinamido)-N,N-diethyl-4-methoxy-3,5-dimethyl-1',3'-dihydrospiro[cyclohexane-1, 2'-indene]-1'-carboxamide give compound 27 (8.50 g, 76%, 98.2 wt. % purity, >99.5% diastereomeric purity) as a white solid.

Example 15

Preparation of Compound 28

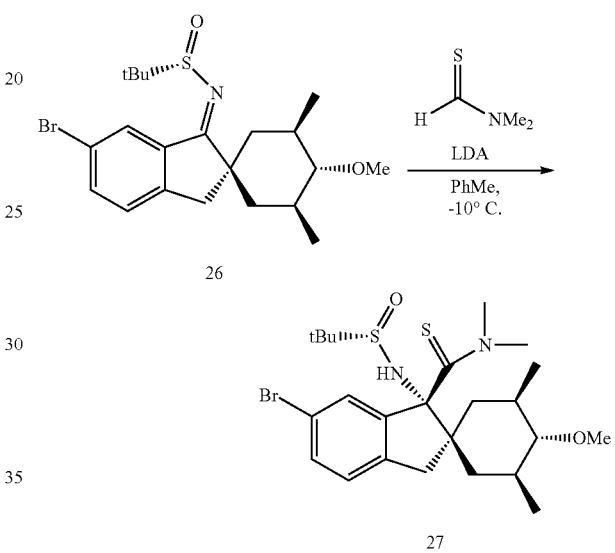

A solution of sulfinimine 26 (2.0 g, 4.54 mmol and N,N-dimethylthioformamide (0.77 mL, 9.08 mmol) in toluene (12 mL) is cooled to −10° C. LDA solution (4.54 mL, 9.08 mmol, 2.0M in THF/heptane/ethylbenzene) is then added dropwise to the reaction mixture at −10° C. Water is added, and the reaction mixture is warmed to about 25° C. Ethyl acetate is added, and the layers are separated. The organic phase is dried over sodium sulfate, filtered, and concentrated by distillation at reduced pressure to give the crude product. ¹H NMR analysis of the crude product shows a diastereomeric ratio of 96:4. The crude product is purified by flash column chromatography on SiO₂ using hexanes/ethyl acetate as eluent to give the diastereomerically pure product 28 as a light brown oil. Yield: 2.02 g, 84.0%.

What is claimed is:

1. A process for making a compound of formula (I):

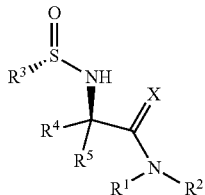

(I)

the process comprising reacting a compound of formula (II):

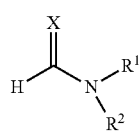

(II)

with lithium diisopropylamide to provide a first intermediate; and reacting the first intermediate with a compound of formula (III):

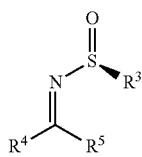

(III)

to provide the compound of formula (I), wherein
X is selected from oxygen and sulfur;
$R^1$ and $R^2$ are each independently selected from —$(C_1-C_6)$ alkyl and phenyl;
or
$R^1$ and $R^2$ may join to form a group selected from cyclopentyl, cyclohexyl, and a 5- to 6-membered heterocyloalkyl;
$R^3$ is t-butyl or 2,4,6-triisopropylphenyl;
$R^4$ is selected from H, —$(C_1-C_6)$alkyl, —$(C_3-C_6)$cycloalkyl, a bicycloalkyl, a tricyloalkyl, and phenyl; wherein each of the foregoing —$(C_1-C_6)$alkyl, —$(C_3-C_6)$cycloalkyl, bicycloalkyl, tricyloalkyl, and phenyl $R^4$ groups is optionally substituted by 1 to 3 $R^6$ groups;
$R^5$ is selected from t-butyl, phenyl, —C═C(R)-phenyl, and —C≡C-phenyl; wherein each of the foregoing t-butyl, phenyl, —C═C(R)-phenyl, and —C≡C-phenyl of said $R^5$ group is optionally substituted by 1 to 3 $R^6$ groups;
or
$R^4$ and $R^5$ may join to form a group selected from cyclobutyl, cyclopentyl, cyclohexyl or dihydroindenyl, wherein each of the foregoing cyclobutyl, cyclopentyl, cyclohexyl or dihydroindenyl groups may be optionally substituted by 1 to 3 $R^6$ groups; and/or each of said cyclobutyl, cyclopentyl, cyclohexyl and dihydroindenyl groups may additionally be substituted by a 6-member spirocycloalkyl optionally substituted by 1 to 3 $R^7$ groups;
each $R^6$ is independently selected from halo, hydroxyl, —$(C_1-C_6)$alkyl, and —O—$(C_1-C_6)$alkyl; and
each $R^7$ is independently selected from halo, hydroxyl, —$(C_1-C_6)$alkyl, and —O—$(C_1-C_6)$alkyl.

2. The process of claim 1, wherein X is sulfur.

3. The process of claim 1, wherein the compound of formula (II) is N,N-dimethylmethanethioamide.

4. The process of claim 1, wherein X is oxygen.

5. The compound of claim 1, wherein the compound of formula (II) is selected from dimethyl formamide, diethyl formamide, isopropyl formamide, diphenyl formamide, pyrrolidine-1-carbaldehyde, and morpholine-4-carbaldehyde.

6. The process of claim 1, wherein $R^3$ is t-butyl.

7. The process of claim 1, wherein $R^3$ is 2,4,6-triisopropylphenyl.

8. The process of claim 1, wherein:
$R^4$ is selected from H, —$(C_1-C_6)$alkyl, —$(C_3-C_6)$cycloalkyl, a bicycloalkyl, a tricyloalkyl, and phenyl; wherein each of the foregoing —$(C_1-C_6)$alkyl, —$(C_3-C_6)$cycloalkyl, bicycloalkyl, tricyloalkyl, and phenyl $R^4$ groups is optionally substituted by 1 to 3 $R^6$ groups; and
$R^5$ is selected from t-butyl, phenyl, —C═C(R)-phenyl, and —C≡C-phenyl; wherein each of the foregoing $R^5$ groups is optionally substituted by 1 to 3 $R^6$ groups.

9. The process of claim 1, wherein $R^4$ is hydrogen.

10. The process of claim 1, wherein $R^4$ is selected from t-butyl, trifluoromethyl, cyclopropyl, cyclohexyl, phenyl, and a group of formula 9-A,

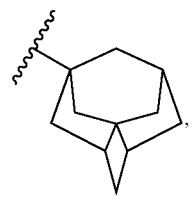

9-A wherein each of the foregoing $R^4$ group is optionally substituted by 1 to 3 $R^6$ groups.

11. The process of claim 1, wherein $R^4$ and $R^5$ join to form a group selected from cyclobutyl, cyclopentyl, cyclohexyl or dihydroindenyl, wherein each of the foregoing cyclobutyl, cyclopentyl, cyclohexyl or dihydroindenyl groups may be optionally substituted by 1 to 3 $R^6$ groups; and/or each of said cyclobutyl, cyclopentyl, cyclohexyl and dihydroindenyl groups may additionally be substituted by a 6-member spirocycloalkyl optionally substituted by 1 to 3 $R^7$ groups.

12. The process of claim 1, wherein $R^4$ and $R^5$ join to form the group:

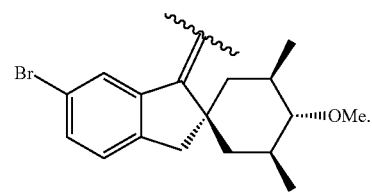 [SMILES: *=C1c2cc(Br)ccc2C[C@@]12C[C@@H](C)[C@H](OC)[C@@H](C)C2]

13. A process for making a compound of formula (27):

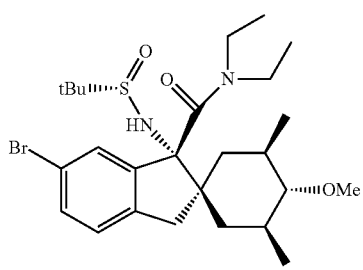

27 the process comprising reacting N,N-diethylformamide with lithium diisopropylamide in the presence of a compound of formula (26):

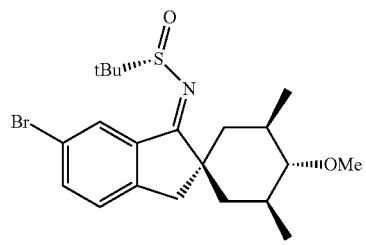
to provide the compound of formula (27).
\* \* \* \* \*